US006866866B1

(12) United States Patent
Chen et al.

(10) Patent No.: US 6,866,866 B1
(45) Date of Patent: *Mar. 15, 2005

(54) CONTROLLED RELEASE METFORMIN COMPOSITIONS

(75) Inventors: Chih-Ming Chen, Davie, FL (US); Xiu-Xiu Cheng, Davie, FL (US); Steve Jan, Coral Springs, FL (US); Joseph Chou, Manassas, VA (US)

(73) Assignee: Andrx Labs, LLC, Davie, FL (US)

( * ) Notice: Subject to any disclaimer, the term of this patent is extended or adjusted under 35 U.S.C. 154(b) by 162 days.

This patent is subject to a terminal disclaimer.

(21) Appl. No.: 09/705,630

(22) Filed: Nov. 3, 2000

(51) Int. Cl.[7] .............................. A61K 9/22; A61K 9/52
(52) U.S. Cl. ...................... 424/468; 424/457; 424/474; 424/480
(58) Field of Search ................................ 424/473, 468, 424/474, 475, 479, 480, 482; 514/635, 588, 591, 592, 593

(56) References Cited

U.S. PATENT DOCUMENTS

| | | | | |
|---|---|---|---|---|
| 3,845,770 A | * | 11/1974 | Theeuwes et al. | 424/427 |
| 5,688,518 A | | 11/1997 | Ayer et al. | 424/422 |
| 5,691,386 A | | 11/1997 | Inman et al. | 514/691 |
| 5,858,398 A | | 1/1999 | Cho | 424/450 |
| 5,955,106 A | * | 9/1999 | Moeckel et al. | 424/464 |
| 6,010,718 A | | 1/2000 | Al-Razzak et al. | 424/464 |
| 6,099,859 A | * | 8/2000 | Cheng et al. | 424/464 |
| 6,099,862 A | * | 8/2000 | Chen et al. | 424/473 |
| 6,284,275 B1 | * | 9/2001 | Chen et al. | 424/473 |
| 6,475,521 B1 | | 11/2002 | Timmins et al. | 424/469 |

FOREIGN PATENT DOCUMENTS

| | | | | |
|---|---|---|---|---|
| WO | WO 99/47125 | * | 9/1999 | |
| WO | WO 9947125 A1 | * | 9/1999 | A61K/9/20 |
| WO | 9947125 | | 9/1999 | A61K/9/20 |
| WO | WO 00/28989 | * | 5/2000 | |
| WO | WO 0028989 A1 | * | 5/2000 | A61K/31/353 |

OTHER PUBLICATIONS

Chiao, C. Sustained–Release Drug Delivery Systems Remington: The Science and Practice of Pharmacy, 1995, Mack Publishing Company, Easton, PA pp. 1660–1669.*

* cited by examiner

*Primary Examiner*—Thurman K. Page
*Assistant Examiner*—Micah Paul Young
(74) *Attorney, Agent, or Firm*—Davidson, Davidson & Kappel, LLC

(57) ABSTRACT

A composition for treating patients having non-insulin-dependent diabetes mellitus (NIDDM) by administering a controlled release oral solid dosage form containing preferably a biguanide drug such as metformin, on a once-a-day basis. The dosage form provides a mean time to maximum plasma concentration ($T_{max}$) of the drug which occurs at 5.5 to 7.5 hours after oral administration on a once-a-day basis to human patients. Preferably, the dose of drug is administered at dinnertime to a patient in the fed state.

25 Claims, 8 Drawing Sheets

CONTROLLED RELEASE METFORMIN COMPOSITIONS

BACKGROUND OF THE INVENTION

The present invention relates to controlled release unit dose formulations containing an antihyperglycemic drug. More specifically, the present invention relates to an oral dosage form comprising a biguanide such as metformin or buformin or a pharmaceutically acceptable salt thereof such as metformin hydrochloride or the metformin salts described in U.S. Pat. Nos. 3,957,853 and 4,080,472 which are incorporated herein by reference.

In the prior art, many techniques have been used to provide controlled and extended-release pharmaceutical dosage forms in order to maintain therapeutic serum levels of medicaments and to minimize the effects of missed doses of drugs caused by a lack of patient compliance.

In the prior art are extended release tablets which have an osmotically active drug core surrounded by a semipermeable membrane. These tablets function by allowing a fluid such as gastric or intestinal fluid to permeate the coating membrane and dissolve the active ingredient so it can be released through a passageway in the coating membrane or if the active ingredient is insoluble in the permeating fluid, pushed through the passageway by an expanding agent such as a hydrogel. Some representative examples of these osmotic tablet systems can be found in U.S. Pat. Nos. 3,845,770, 3,916,899, 4,034,758, 4,077,407 and 4,783,337. U.S. Pat. No. 3,952,741 teaches an osmotic device wherein the active agent is released from a core surrounded by a semipermeable membrane only after sufficient pressure has developed within the membrane to burst or rupture the membrane at a weak portion of the membrane.

The basic osmotic device described in the above cited patents have been refined over time in an effort to provide greater control of the release of the active ingredient. For example U.S. Pat. Nos. 4,777,049 and 4,851,229 describe an osmotic dosage form comprising a semipermeable wall surrounding a core. The core contains an active ingredient and a modulating agent wherein the modulating agent causes the active ingredient to be released through a passageway in the semipermeable membrane in a pulsed manner. Further refinements have included modifications to the semipermeable membrane surrounding the active core such as varying the proportions of the components that form the membrane; i.e., U.S. Pat. Nos. 5,178,867, 4,587,117 and 4,522,625 or increasing the number of coatings surrounding the active core; i.e., U.S. Pat. Nos. 5,650,170 and 4,892,739.

Although vast amounts of research has been performed on controlled or sustained release compositions and in particular on osmotic dosage forms, very little research has been performed in the area of controlled or sustained release compositions that employ antihyperglycemic drugs.

Metformin is an oral antihyperglycemic drug used in the management of non-insulin-dependent diabetes mellitus (NIDDM). It is not chemically or pharmacologically related to oral sulfonylureas. Metformin improves glucose tolerance in NIDDM patients by lowering both basal and postprandial plasma glucose. Metformin hydrochloride is currently marketed as GLUCOPHAGE® tablets by Bristol-Myers Squibb Co. Each GLUCOPHAGE® tablet contains 500, 850 or 1000 mg of metformin hydrochloride. There is no fixed dosage regimen for the management of hyperglycemia in diabetes mellitus with GLUCOPHAGE®. Dosage of GLUCOPHAGE® is individualized on the basis of both effectiveness and tolerance, while not exceeding the maximum recommended dose of 2550 mg per day.

Metformin has been widely prescribed for lowering blood glucose in patients with NIDDM. However, being a short acting drug, metformin requires twice-daily (b.i.d.) or three-times-a-day (t.i.d.) dosing. Adverse events associated with metformin use are often gastrointestinal in nature (e.g., anorexia, nausea, vomiting and occasionally diarrhea, etc.). These adverse events may be partially avoided by either reducing the initial and/or maintenance dose or using an extended-release dosage form. Another clear advantage of an extended release dosage form is a reduction in the frequency of administration. All of these findings suggest that an extended-release dosage form of metformin may improve the quality of therapy in patients with NIDDM and the safety profile relative to a conventional dosage form.

The limited work on controlled or sustained release formulations that employ antihyperglycemic drugs such as metformin hydrochloride includes the combination of the antihyperglycemic drug and an expanding or gelling agent to control the release of the drug from the dosage form. This research is exemplified by the teachings of WO 96/08243 and by the GLUCOPHAGE® metformin HCl product.

It is reported in the $50^{th}$ Edition of the Physicians' Desk Reference, copyright 1996, p. 753, that food decreases the extent and slightly delays the absorption of metformin delivered by the GLUCOPHAGE® dosage form. This decrease is shown by approximately a 40% lower peak concentration, a 25% lower bioavailability and a 35-minute prolongation of time to peak plasma concentration following administration of a single GLUCOPHAGE® tablet containing 850 mg of metformin HCl with food compared to the similar tablet administered under fasting conditions.

A controlled release metformin dosage form is also described in WO 99/47128. This a reference describes a controlled release delivery system for metformin which includes an inner solid particulate phase formed of substantially uniform granules containing metformin and one or more hydrophilic polymers, one or more hydrophobic polymers and one or more hydrophobic materials, and an outer continuous phase in which the above granules are embedded and dispersed throughout. The outer continuous phase includes one or more hydrophilic polymers, one or more hydrophobic polymers and one or more hydrophobic materials.

Our own WO 99/47125 discloses controlled release metformin formulations providing a Tmax from 8 to 12 hours.

OBJECTS AND SUMMARY OF THE INVENTION

It is an object of the present invention to provide a controlled or sustained release of an antihyperglycemic drug which provides effective control of blood glucose levels in humans.

It is a further object of the present invention to provide a method of treating human patients with non-insulin-dependent diabetes mellitus (NIDDM) on a once-a-day basis with an antihyperglycemic drug which provides effective control of blood glucose levels in humans.

It is a further object of the present invention to provide formulations for treating human patients with non-insulin-dependent diabetes mellitus (NIDDM) which provides advantages over the state-of-the-art, and which may be administered on a once-a-day basis by itself or together with other antidiabetic agents, and methods thereof.

It is a further object of the present invention to provide a controlled or sustained release formulation of an antihyperglycemic drug wherein the bioavailability of the drug is not decreased by the presence of food.

It is a further object of the present invention to provide a controlled or sustained release formulation of an antihyperglycemic drug that does not employ an expanding polymer.

It is also a further object of the present invention to provide a controlled or sustained release formulation of an antihyperglycemic drug that can provide continuous and non-pulsating therapeutic levels of the drug to an animal or human in need of such treatment over a twelve hour to twenty-four hour period.

It is an additional object of other embodiments of the present invention to provide a controlled or sustained release formulation for an antihyperglycemic drug that obtains peak plasma levels from 5.5 to 7.5 hours after administration under various conditions. Alternatively, the time to peak plasma levels are from 6.0 to 7.0, from 5.5 to 7.0 or from 6.0 to 7.5.

It is also an object of this invention to provide a controlled or sustained release pharmaceutical formulation having a homogeneous core wherein the core component may be made using ordinary tablet compression techniques.

In accordance with the above-mentioned objects and others, the present invention provides a controlled release oral dosage form comprising an antihyperglycemic drug, preferably a biguanide (e.g., metformin or a pharmaceutically acceptable salt thereof) that is suitable for providing once-a-day administration of the drug, wherein the dosage form provides a mean time to maximum plasma concentration ($T_{max}$) of the drug from 5.5 to 7.5 hours after administration. The dosage form comprises the drug and a membrane. In certain preferred embodiments, the dosage form comprises a tablet.

In preferred embodiments, the controlled release oral dosage form of the present invention is a tablet comprising:
(a) a core comprising:
    (i) the antihyperglycemic drug;
    (ii) optionally a binding agent; and
    (iii) optionally an absorption enhancer;
(b) a membrane coating surrounding the core; and
(c) at least one passageway in the membrane.

When the drug is metformin or a pharmaceutically acceptable salt thereof and is administered on a once-a-day basis, the daily dose may vary, e.g., from about 500 mg to about 2500 mg. Such daily dose may be contained in one controlled-release dosage form of the invention, or may be contained in more than one such dosage form. For example, a controlled-release metformin dosage form may be formulated to contain about 1000 mg of the drug, and two of said dosage form may be administered together to provide once-a-day metformin therapy. The daily dose of the drug (i.e. metformin or pharmaceutically acceptable salt thereof) may range from about 500 mg to about 2500 mg, from about 1000 mg to about 2500 mg, or from about 2000 mg to about 2500 mg, depending on the clinical needs of the patient.

In certain preferred embodiments, the controlled release solid oral dosage form of the present invention provides a width at 50% of the height of a mean plasma concentration/time curve of the drug (e.g., of metformin) from about 4.5 to about 13 hours, more preferably from about 5.5 to about 10 hours, more preferably from about 6 to about 8 hours.

In certain embodiments, the controlled release oral dosage form of the present invention provides a mean maximum plasma concentration ($C_{max}$) of the antihyperglycemic drug which is more than about seven times the mean plasma level of said drug at about 24 hours after administration. In preferred embodiments, the controlled release oral dosage form of the present invention provides a mean maximum plasma concentration ($C_{max}$) of the drug which is from about 7 times to about 14 times the plasma level of the drug at about 24 hours after the administration, more preferably from about 8 times to about 12 times the plasma level of the drug at about 24 hours after administration.

In certain embodiments of the present invention, when the drug is metformin or a pharmaceutically acceptable salt thereof, the controlled release oral dosage form provides a mean maximum plasma concentration ($C_{max}$) of the drug that is about 1500 ng/ml to about 3000 ng/ml, based on administration of a 2000 mg once-a-day dose of metformin, more preferably about 1700 ng/ml to about 2000 ng/ml, based on administration of a 2000 mg once-a-day dose of metformin.

In certain embodiments of the present invention, when the drug is metformin or a pharmaceutically acceptable salt thereof, the controlled release dosage form provides a mean $AUC_{0-24hr}$ that is about 17200 ng.hr/ml to about 33900 ng.hr/ml, based on administration of a 2000 mg once-a-day dose of metformin; preferably about 17200 ng.hr/ml to about 26500 ng.hr/ml, based on administration of a 2000 mg once-a-day dose of metformin; more preferably about 19800 ng.hr/ml to about 33900 ng.hr/ml, based on administration of a 2000 mg once-a-day dose of metformin.

In certain embodiments of the invention, the administration of the antihyperglycemic drug, e.g., at least one metformin dosage form provides a mean $AUC_{0-24hr}$ from at least 80%, preferably at least 90% of the mean $AUC_{0-24}$ provided by administration of the reference standard (GLUCOPHAGE) twice a day, wherein the daily dose of the reference standard is equal to the once-a day dose of metformin administered in the controlled release oral dosage form of the present invention.

In certain embodiments of the present invention, the controlled release dosage form exhibits the following dissolution profiles of the antihyperglycemic drug (e.g., metformin) when tested in a USP type 2 apparatus at 75 rpm in 900 ml of simulated intestinal gastric fluid (pH 7.5 phosphate buffer) at 37° C.: 0–30% of the drug released after 2 hours; 10–45% of the drug released after 4 hours; 30–90% of the drug released after 8 hours; not less than 50% of the drug released after 12 hours; not less than 60% of the drug released after 16 hours; and not less than 70% of the drug released after 20 hours.

In certain preferred embodiments, the controlled release solid oral dosage form exhibits the following dissolution profiles when tested in USP type 2 apparatus at 75 rpm in 900 ml of simulated intestinal gastric fluid (pH 7.5 phosphate buffer) at 37° C.: 0–25% of the drug (e.g., metformin or a pharmaceutically acceptable salt thereof) released after 2 hours; 20–40% of the drug released after 4 hours; 45–90% of the drug released after 8 hours; not less than 60% of the drug released after 12 hours; not less than 70% of the drug released after 16 hours; and not less than 80% of the drug released after 20 hours.

With respect to embodiments of the present invention where the antihyperglycemic drug is metformin, it has been found that drugs such as metformin provide substantially linear pharmacokinetics up to a level of about 2 grams per day. Therefore, it is contemplated for purposes of the present invention that a given plasma level (e.g., $C_{max}$) of metformin per specified dose will be directly proportional to other doses of metformin. Such proportional doses and plasma levels are contemplated to be within the scope of the invention and to be within the scope of the appended claims.

The dosage form of the present invention can provide therapeutic levels of the antihyperglycemic drug for twelve to twenty-four hour periods and does not exhibit a decrease in bioavailability if taken with food. In fact, a slight increase in the bioavailability of the antihyperglycemic drug is observed when the controlled release dosage form of the present invention is administered with food. In a preferred embodiment, the dosage form can be administered once-a-day, ideally with or after a meal, preferably with or after the evening meal, and provides therapeutic levels of the drug throughout the day with peak plasma levels being obtained between 5.5 to 7.5 hours after administration.

The present invention is also directed to a method of lowering blood glucose levels in human patients needing treatment for non-insulin-dependent diabetes mellitus (NIDDM), comprising orally administering to human patients on a once-a-day basis a dose of a drug comprising a biguanide (e.g., metformin or a pharmaceutically acceptable salt thereof), said drug being contained in at least one solid oral controlled release dosage form of the present invention. When the drug is metformin, the daily dose of the drug may be from about 500 mg to about 2500 mg, from about 1000 mg to about 2500 mg, or from about 2000 mg to about 2500 mg, depending on the clinical needs of the patient.

The controlled release dosage form of the present invention provides a delayed $T_{max}$, as compared to the $T_{max}$ provided by GLUCOPHAGE. The delayed $T_{max}$ occurs from 5.5 to 7.5 hours after administration. If the drug (e.g., metformin) is administered at dinner time, the $T_{max}$ would occur during the time when gluconeogenesis is usually at its highest (e.g., around 2 a.m.).

The present invention also includes a method of treating patients with NIDDM comprising orally administering to human patients on a once-a-day basis a dose of a drug comprising a biguanide (e.g., metformin or a pharmaceutically acceptable salt thereof), contained in at least one oral controlled release dosage form of the present invention. When the drug is metformin, the daily dose of the drug maybe from about 500 mg to about 2500 mg, from about 1000 mg to about 2500 mg, or from about 2000 mg to about 2500 mg, depending on the clinical needs of the patient. In certain embodiments, the method of treatment according to the present invention involves once-per-day metformin monotherapy as an adjunct to diet to lower blood glucose in patients with NIDDM whose hyperglycemia may not be satisfactorily managed on diet alone. In certain other embodiments, the once-a-day metformin therapy of the present invention may be used concomitantly with a sulfonylurea, e.g., when diet and monotherapy with a sulfonylurea alone do not result in adequate glycemic control. In certain other embodiments, the once-a-day metformin therapy of the present invention may be used concomitantly with a glitazone, e.g., when diet and monotherapy with a glitazone alone do not result in adequate glycemic control.

The present invention is further directed to a method of controlling the serum glucose concentration in human patients with NIDDM, comprising administering to patients having NIDDM on a once-a-day basis, preferably at dinner time, an effective dose of a biguanide (e.g., metformin) contained in at least one oral controlled release dosage form of the present invention.

The present invention further includes a controlled-release dosage form of a drug comprising a biguanide (e.g., metformin) suitable for once-a-day administration to human patients with NIDDM, the dosage form comprising an effective amount of the drug to control blood glucose levels for up to about 24 hours and an effective amount of a controlled-release carrier to provide controlled release of the drug with a mean time to maximum plasma concentration ($T_{max}$) of the drug from 5.5 to 7.5 hours after administration and a width at 50% of the height of a mean plasma concentration/time curve of the drug from about 6 to about 13 hours. In preferred embodiments, the administration of the controlled-release dosage form occurs at fed state, more preferably at dinner time.

In certain preferred embodiments, the controlled-release dose of the drug (e.g., metformin or a pharmaceutically acceptable salt thereof) according to the present invention is provided by one or more of a controlled-release tablet comprising
  (a) a core comprising:
    (i) the antihyperglycemic drug (e.g., metformin or a pharmaceutically acceptable salt thereof);
    (ii) optionally a binding agent; and
    (iii) optionally an absorption enhancer;
  (b) a membrane coating surrounding the core; and
  (c) at least one passageway in the membrane.

In certain preferred embodiments, the mean time to maximum plasma concentration of the drug is reached from 6.5 to 7.5 hours after administration at dinner time.

In certain embodiments of the invention when the drug is a biguanide (e.g. metformin or a pharmaceutically acceptable salt thereof), the controlled release dosage form provides upon single administration, a higher mean fluctuation index in the plasma than an equivalent dose of an immediate release composition administered as two equal divided doses, one divided dose at the start of the dosing interval and the other divided dose administered 12 hours later, preferably maintaining bioavailability from at least 80% preferably from at least 90% of the immediate release composition.

In certain embodiments of the present invention, the mean fluctuation index of the dosage form is from about 1 to about 4, preferably about 2 to about 3, more preferably about 2.5.

In certain embodiments of the invention which exhibit a higher mean fluctuation index in the plasma than an equivalent dose of an immediate release composition administered as two equal divided doses, the ratio of the mean fluctuation index between the dosage form and the immediate release composition is about 3:1, preferably about 2:1, more preferably 1.5:1.

When the drug is metformin or a pharmaceutically acceptable salt thereof, the doses of drug which exhibit the above disclosed mean fluctuation indexes can be any effective dose administered to a patient with NIDDM for the reduction of serum glucose levels. For example, the dose can from about 500 mg to about 2500 mg, from about 1000 mg to about 2000 mg or from about 850 mg to about 1700 mg metformin or pharmaceutically acceptable salt thereof.

The drugs which may used in conjunction with the present invention include those drugs which are useful for the treatment of non-insulin-dependent diabetes mellitus (NIDDM), including but not limited to biguinides such as metformin or buformin or pharmaceutically acceptable salts thereof. When the drug used in the present invention is metformin, it is preferred that the metformin be present in a salt form, preferably as metformin hydrochloride.

The term "metformin" as it is used herein means metformin base or any pharmaceutically acceptable salt e.g., metformin hydrochloride.

The term "dosage form" as it is used herein means at least one unit dosage form of the present invention (e.g. the daily dose of the antihyperglycemic agent can be contained in 2 unit dosage forms of the present invention for single once-a-day administration).

The term "morning" as it is used herein with respect to the dosing of the controlled release formulations of the invention means that the controlled release formulation is orally administered early in the day after the patient has awakened from overnight sleep, generally between about 6 a.m. and 11 a.m. (regardless of whether breakfast is eaten at that time, unless so specified herein).

The term "dinnertime" or "at dinner" as it is used herein with respect to the dosing of the controlled release formulations of the invention means that the controlled release formulation is orally administered at a time when dinner is normally eaten (regardless of whether a meal is actually eaten at that time, unless so specified herein), generally between about 4 p.m. and 8 p.m.

The term "bedtime" as it is used herein with respect to the dosing of the controlled release formulations of the invention means that the controlled release formulation is orally administered before the patient goes to bed in the evening, generally between about 8 p.m. and 12 p.m.

The term "therapeutically effective reduction" when used herein is meant to signify that blood glucose levels are reduced by approximately the same amount as an immediate release reference standard (e.g., GLUCOPHAGE®) or more, when the controlled release dosage form is orally administered to a human patient on a once-a-day basis.

The term "sustained release" and "controlled release" are used interchangeably in this application and are defined for purposes of the present invention as the release of the drug from the dosage form at such a rate that when a once-a-day dose of the drug is administered in the sustained release or controlled-release form, blood (e.g., plasma) concentrations (levels) of the drug are maintained within the therapeutic range but below toxic levels over a period of time from about 12 to about 24 hours. When the drug used in the present invention is metformin (preferably metformin hydrochloride) the controlled release solid oral dosage form containing such drug is also referred to as "Metformin XT."

The term "$C_{max}$" is the highest plasma concentration of the drug attained within the dosing interval, i.e., about 24 hours.

The term "$C_{min}$" is the minimum plasma concentration of the drug attained within the dosing interval, i.e. about 24 hours.

The term "$C_{avg}$" as used herein, means the plasma concentration of the drug within the dosing interval, i.e. about 24-hours, and is calculated as AUC/dosing interval.

The term "$T_{max}$" is the time period which elapses after administration of the dosage form at which the plasma concentration of the drug attains the highest plasma concentration of drug attained within the dosing interval (i.e., about 24 hours).

The term "AUC" as used herein, means area under the plasma concentration-time curve, as calculated by the trapezoidal rule over the complete 24-hour interval.

The term "steady state" means that the blood plasma concentration curve for a given drug does not substantially fluctuate after repeated doses to dose of the formulation.

The term "single dose" means that the human patient has received a single dose of the drug formulation and the drug plasma concentration has not achieved steady state.

The term "multiple dose" means that the human patient has received at least two doses of the drug formulation in accordance with the dosing interval for that formulation (e.g., on a once-a-day basis). Patients who have received multiple doses of the controlled release formulations of the invention may or may not have attained steady state drug plasma levels, as the term multiple dose is defined herein.

The term "a patient" means that the discussion (or claim) is directed to the pharmacokinetic parameters of an individual patient and/or the mean pharmacokinetic values obtained from a population of patients, unless further specified.

The term "mean", when preceding a pharmacokinetic value (e.g. mean $T_{max}$) represents the arithmetic mean value of the pharmacokinetic value taken from a population of patients unless otherwise specified (e.g. geometric mean).

The term "Degree of Fluctuation" is expressed as $(C_{max}-C_{min})/C_{avg}$.

DETAILED DESCRIPTION OF THE INVENTION

Figure 1:
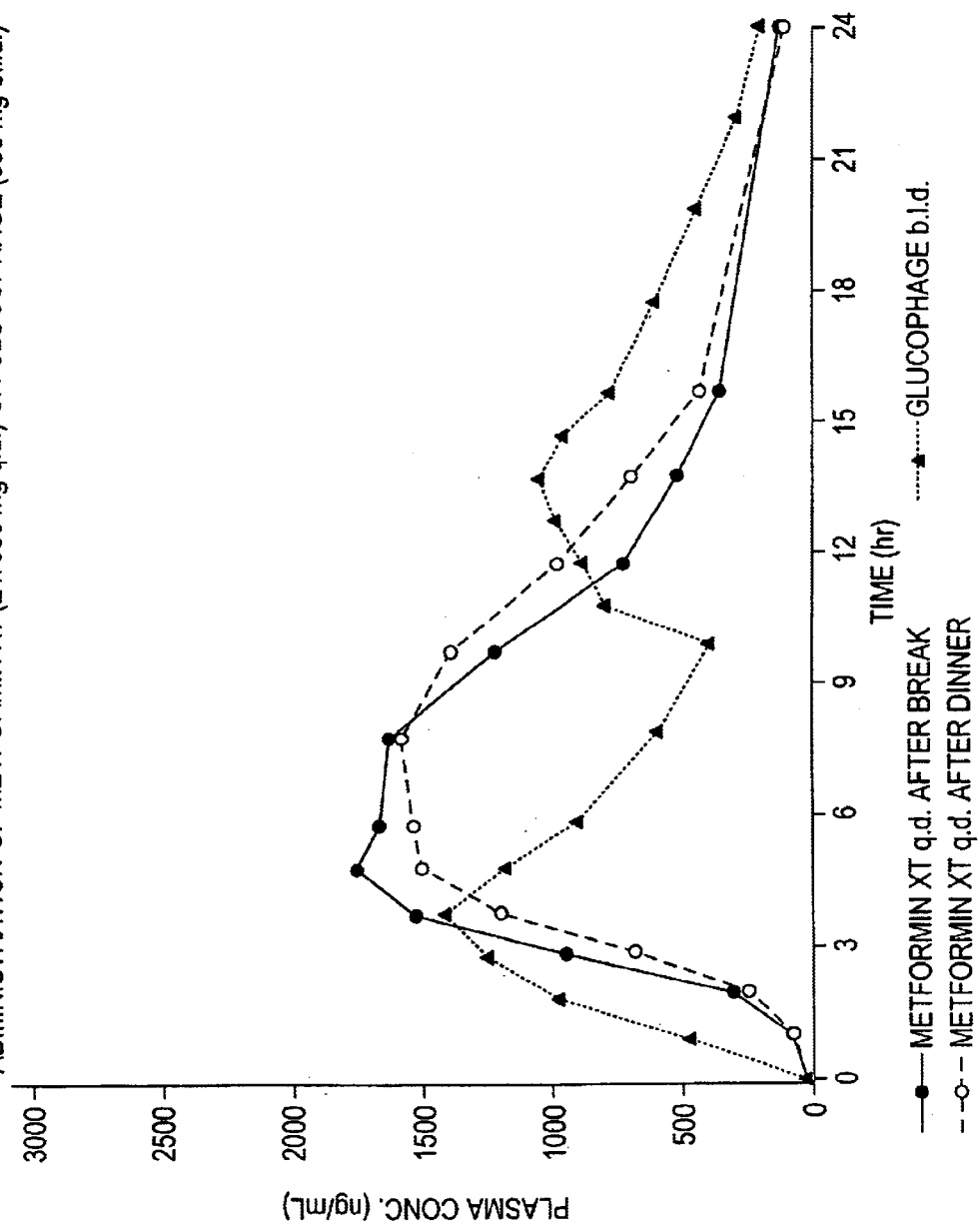
FIG. 1 is a graph showing the relative bioavailability of the metformin XT formulation of Example 2 to GLUCOPHAGE® for Clinical Study 2.

The term antihyperglycemic drugs as used in this specification refers to drugs that are useful in controlling or managing noninsulin-dependent diabetes mellitus (NIDDM). Preferably, the antihyperglycemic drug is a biguanide such as metformin or buformin or a pharmaceutically acceptable salt thereof such as metformin hydrochloride.

It has surprisingly been found that when biguanides such as metformin are administered orally in a controlled release dosage form suitable for once-a-day dosing in the "fed" state, preferably at dinner, the bioavailability is improved as compared to the administration of the controlled release dosage form in the "fasted" state. This is in contrast to GLUCOPHAGE®, which exhibits opposite characteristics. In accordance with the methods and dosage forms of the present invention, it has been determined that the patients suffering from NIDDM achieve improved results (e.g., lowered blood glucose levels) than GLUCOPHAGE® administered according to accepted protocols, e.g., on a twice-a-day basis.

The methods and dosage forms of the invention provide the further advantage in that when dosed at dinnertime, the controlled release formulations of the invention provide a $T_{max}$ (from 5.5 to 7.5 hours) after oral administration (which $T_{max}$ is delayed relative to the reference standard, GLUCOPHAGE®), such that the level of drug is greatest at the time when human patients are manufacturing glucose at highest levels. Gluconeogenesis is well known to those skilled in the art to be greatest at night. Thus, in accordance with the invention, the $T_{max}$ of the drug occurs for example between 11:30 p.m. and 1:30 a.m., based on a dose administered at 6:00 p.m. Likewise, such administration of the dosage form provides lower drug levels during the day (e.g. the afternoon) when gluconeogenesis is lower than at night. Also, the invention preferably provides the added benefit of lowering insulin levels. Insulin is considered a risk factor in NIDDM, in and of itself, for cardiovascular disease.

In comparison to a twice-daily dose of the reference standard (GLUCOPHAGE®), the plasma levels of metformin are preferably lower in the afternoon. This is an advantage particularly in patients who are under concomitant therapy with one or more additional antidiabetic agents, such as for example, a sulfonylurea. It is known in the art that to date approximately 60% of patients being treated with metformin are also being treated with at least one additional antidiabetic agent (such as a sulfonylurea). Sulfonylureas can possibly cause hypoglycemia, whereas metformin cannot, so there is a benefit to having lower metformin levels in the blood during the afternoon due to the potential for the patient to have hypoglycemia.

Accordingly, the present invention also includes a method of treating human patients with NIDDM comprising administering on a once-a-day basis a therapeutically effective dose of metformin in a controlled-release oral dosage form ("Metformin XT"), in combination with administering an effective amount of a sulfonylurea. In preferred embodiments, metformin is provided by a controlled release dosage form comprising metformin or a pharmaceutically acceptable salt thereof, the dosage form being useful for providing a once-a-day oral administration of the drug, wherein the dosage form provides a mean time to maximum plasma concentration ($T_{max}$) of metformin from 5.5 to 7.5 hours after administration.

In certain embodiments, the combination therapy may be provided as follows. If patients do not respond to four weeks of the maximum dose of Metformin XT (2500 mg/day) monotherapy, a sulfonylurea may be gradually added while maintaining the maximum dose of Metformin XT, even if prior primary or secondary failure to a sulfonylurea has occurred. Examples of the sulfonylurea include glyburide (glibenclamid), chloropropamide, tolbutamide, glipizide, acetohexamide and tolazamide. Although Metformin XT is preferably administered on once-a-day basis, the sulfonylurea may be administered in a different dosage form and at a different frequency.

With concomitant Metformin XT and sulfonylurea therapy, the desired control of blood glucose may be obtained by adjusting the dose of each drug.

In certain embodiments, the foregoing objectives are met by a controlled release dosage form comprising:
(a) a core comprising:
  (i) an antihyperglycemic drug;
  (ii) optionally a binding agent; and
  (iii) optionally an absorption enhancer;
(b) a membrane coating surrounding the core; and
(c) at least one passageway in the membrane.

The binding agent may be any conventionally known pharmaceutically acceptable binder such as polyvinyl pyrrolidone, hydroxypropyl cellulose, hydroxyethyl cellulose, ethylcellulose, polymethacrylate, waxes and the like. Mixtures of the aforementioned binding agents may also be used. The preferred binding agents are water soluble such as polyvinyl pyrrolidone having a weight average molecular weight of 25,000 to 3,000,000. The binding agent comprises approximately about 0 to about 40% of the total weight of the core and preferably about 3% to about 15% of the total weight of the core.

The core may optionally comprise an absorption enhancer. The absorption enhancer can be any type of absorption enhancer commonly known in the art such as a fatty acid, a surfactant, a chelating agent, a bile salt or mixtures thereof. Examples of some preferred absorption enhancers are fatty acids such as capric acid, oleic acid and their monoglycerides, surfactants such as sodium lauryl sulfate, sodium taurocholate and polysorbate 80, chelating agents such as citric acid, phytic acid, ethylenediamine tetraacetic acid (EDTA) and ethylene glycol-big (B-aminoethyl ether —N,N,N,N-tetraacetic acid (EGTA). The core comprises approximately 0 to about 20% of the absorption enhancer based on the total weight of the core and most preferably about 2% to about 10% of the total weight of the core.

In this embodiment, the core which comprises the antihyperglycemic drug, the binder which preferably is a pharmaceutically acceptable water soluble polymer and the absorption enhancer is preferably formed by wet granulating the core ingredients and compressing the granules with the addition of a lubricant into a tablet on a rotary press. The core may also be formed by dry granulating the core ingredients and compressing the granules with the addition of a lubricant into tablets or by direct compression.

Other commonly known excipients may also be included into the core such as lubricants, pigments or dyes.

The homogeneous core is coated with a membrane, preferably a polymeric membrane to form the controlled release tablet of the invention. The membrane can be a semipermeable membrane by being permeable to the passage of external fluid such as water and biological fluids and being impermeable to the passage of the antihyperglycemic drug in the core. Materials that are useful in forming the membrane are cellulose esters, cellulose diesters, cellulose triesters, cellulose ethers, cellulose ester-ether, cellulose acylate, cellulose diacylate, cellulose triacylate, cellulose acetate, cellulose diacetate, cellulose triacetate, cellulose acetate propionate, and cellulose acetate butyrate. Other suitable polymers are described in U.S. Pat. Nos. 3,845,770, 3,916,899, 4,008,719, 4,036,228 and 4,11210 which are incorporated herein by reference. The most preferred membrane material is cellulose acetate comprising an acetyl content of 39.3 to 40.3%, commercially available from Eastman Fine Chemicals.

In an alternative embodiment, the membrane can be formed from the above-described polymers and a flux enhancing agent. The flux enhancing agent increases the volume of fluid imbibed into the core to enable the dosage form to dispense substantially all of the antihyperglycemic drug through the passageway and/or the porous membrane. The flux enhancing agent can be a water soluble material or an enteric material. Some examples of the preferred materials that are useful as flux enhancers are sodium chloride, potassium chloride, sucrose, sorbitol, mannitol, polyethylene glycol (PEG), propylene glycol, hydroxypropyl cellulose, hydroxypropyl methycellulose, hydroxyprophy methycellulose phthalate, cellulose acetate phthalate, polyvinyl alcohols, methacrylic acid copolymers and mixtures thereof. The preferred flux enhancer is PEG 400.

The flux enhancer may also be a drug that is water soluble such as metformin or its pharmaceutically acceptable salts or a drug that is soluble under intestinal conditions. If the flux enhancer is a drug, the present dosage form has the added advantage of providing an immediate release of the drug which is selected as the flux enhancer.

The flux enhancing agent comprises approximately 0 to about 40% of the total weight of the coating, most preferably about 2% to about 20% of the total weight of the coating. The flux enhancing agent dissolves or leaches from the membrane to form paths in the membrane for the fluid to enter the core and dissolve the active ingredient.

In alternate embodiments, the membrane may also be formed with commonly known excipients such as a plasticizer. Some commonly known plasticizers include adipate, azelate, enzoate, citrate, stearate, isoebucate, sebacate, triethyl citrate, tri-n-butyl citrate, acetyl tri-n-butyl citrate, citric acid esters, and those described in the Encyclopedia of Polymer Science and Technology, Vol. 10 (1969), published by John Wiley & Sons. The preferred plasticizers are triacetin, acetylated monoglyceride, grape seed oil, olive oil, sesame oil, acetyltributylcitrate, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate, and the like. Depending on the particular plasticizer, amounts of from 0 to about 25%, and preferably about 2% to about 15% of the plasticizer can be used based upon the total weight of the coating.

As used herein the term passageway includes an aperture, orifice, bore, hole, weakened area or an erodible element such as a gelatin plug that erodes to form an osmotic passageway for the release of the antihyperglycemic drug from the dosage form. A detailed description of the passageway can be found in U.S. Pat. Nos. such as 3,845,770, 3,916,899, 4,034,758, 4,063,064, 4,077,407, 4,088,864, 4,783,337 and 5,071,607 (the disclosures of which are hereby incorporated by reference).

In certain embodiments, the passageway is formed by laser drilling. In other embodiments, the passageway is formed by making an indentation onto the core prior to the membrane coating to form a weakened area of the membrane at the point of the indentation. In preferred embodiments of the invention, the dosage form contains two passageways in order provide the desired pharmacokinetic parameters of the formulation.

Generally, the membrane coating around the core will comprise from about 1% to about 7%, preferably about 1.5% to about 3%, based on the total weight of the core and coating.

The term "membrane" means a membrane that is permeable to both aqueous solutions or bodily fluids and to the active drug or pharmaceutical ingredient (e.g. the formulations of Examples 1–3). Thus, the membrane is porous to drug and, in a preferred embodiment, drug is released through the hole or passageway and through the porous membrane in solution or in vivo. The term "membrane" also generically encompasses the term "semipermeable membrane" as heretofore defined.

In an alternative embodiment, the dosage form of the present invention may also comprise an effective amount of the antihyperglycemic drug that is available for immediate release. The effective amount of antihyperglycemic drug for immediate release may be coated onto the membrane of the dosage form or it may be incorporated into the membrane.

In certain preferred embodiments of the invention where the dosage form is prepared in accordance with the above, the dosage form will have the following composition:

| INGREDIENT | Preferred | Most Preferred |
|---|---|---|
| CORE: | | |
| Drug | 50–98% | 75–95% |
| Binder | 0–40% | 3–15% |
| Absorption Enhancer | 0–20% | 2–10% |
| COATING: | | |
| Membrane Polymer | 50–99% | 75–95% |
| Flux Enhancer | 0–40% | 2–20% |
| Plasticizer | 0–25% or 0–30% | 2–15% |

The dosage forms prepared according to certain embodiments of the present invention preferably exhibit the following dissolution profile when tested in a USP type 2 k apparatus at 75 rpms in 900 ml of simulated intestinal fluid (pH 7.5 phosphate buffer) and at 37° C.:

| Time (Hours) | Preferred | Most Preferred |
|---|---|---|
| 2 | 0–30% | 0–15% or 0–25% |
| 4 | 10–45% | 20–40% |
| 8 | 30–90% | 45–90% |
| 12 | NTL 50% | NTL 60% |
| 16 | NTL 60% | NTL 70% |
| 20 | NTL 70% | NTL 80% |

NTL = Not less than

In the preparation of the tablets of the invention, various conventional well known solvents may be used to prepare the granules and apply the external coating to the tablets of the invention. In addition, various diluents, excipients, lubricants, dyes, pigments, dispersants, etc. which are disclosed in Remington's Pharmaceutical Sciences, 1995 Edition may be used to optimize the formulations of the invention.

Other controlled release technologies known to those skilled in the art can be used in order to achieve the controlled release formulations of the present invention, i.e., formulations which provide a mean $T_{max}$ of the drug and/or other pharmacokinetic parameters described herein when orally administered to human patients. Such formulations can be manufactured as a controlled oral formulation in a suitable tablet or multiparticulate formulation known to those skilled in the art. In either case, the controlled release dosage form may optionally include a controlled release carrier which is incorporated into a matrix along with the drug, or which is applied as a controlled release coating.

An oral dosage form according to the invention may be provided as, for example, granules, spheroids, beads, pellets (hereinafter collectively referred to as "multiparticulates") and/or particles. An amount of the multiparticulates which is effective to provide the desired dose of drug over time may be placed in a capsule or may be incorporated in any other suitable oral form.

In certain preferred embodiments, the tablet core or multiparticulates containing the drug are coated with a hydrophobic material selected from (i) an alkylcellulose and (ii) a polymeric glycol. The coating may be applied in the form of an organic or aqueous solution or dispersion. The coating may be applied to obtain a weight gain from about 2 to about 25% of the substrate in order to obtain a desired sustained release profile. The sustained release coatings of the present invention may also include an exit means comprising at least one passageway, orifice, or the like as previously disclosed.

Description of Certain Preferred Embodiments

The following examples illustrate various aspects of the present invention. They are not to be construed to limit the claims in any manner whatsoever.

EXAMPLE 1

A controlled release tablet containing 500 mg of metformin HCl and having the following formula is prepared as follows:

| I. Core | |
|---|---|
| Ingredients | Amount (mg/tab) |
| Metformin HCl | 500.0 |
| Povidone[3], USP | 36.0 |
| Sodium Lauryl Sulfate | 25.8 |
| Magnesium Stearate | 2.8 |

[3]approximate molecular weight = 1,000,000; dynamic viscosity (10% w/v solution at 20° C.) = 300–700 m Pa s.

(a) Granulation

The metformin HCl and sodium lauryl sulfate are delumped by passing them through a 40 mesh screen and collecting them in a clean, polyethylene-lined container. The povidone, K-90-F is dissolved in purified water. The delumped metformin HCl and sodium lauryl sulfate are then added to a top-spray fluidized bed granulator and granulated by spraying with the binding solution of povidone under the following conditions: inlet air temperature of 50–70° C.; atomization air pressure of 1–3 bars; and spray rate of 10–100 ml/min.

Once the binding solution is depleted, the granules are dried in the granulator until the loss on drying is less than 2%. The dried granules are passed through a Comil equipped with the equivalent of an 18 mesh screen.

(b) Tableting

The magnesium stearate is passed through a 40 mesh stainless steel screen and blended with the metformin HCl granules for approximately five (5) minutes. After blending, the granules are compressed on a rotary press fitted with 15/32" round standard concave punches.

(c) Seal Coating (Optional)

The core tablet is seal coated with an Opadry material or other suitable water-soluble material by first dissolving the Opadry material, preferably Opadry Clear (YS-1-7006), in purified water. The Opadry solution is then sprayed onto the core tablet using a pan coater under the following conditions: exhaust air temperature of 38–42° C.; atomization pressure of 28–40 psi; and spray rate of 10–15 ml/min. The Opadry Clear of the coating constitutes about 11.5 mg/tablet.

| II. Sustained Release Coating | |
|---|---|
| Ingredients | Amount (mg/tablet) |
| Cellulose Acetate (398-10)[2] | 21.5 |
| Triacetin | 1.3 |
| PEG 400 | 2.5 |

[2]acetyl content 39.3–40.3%

The cellulose acetate is dissolved in acetone while stirring with a homogenizer. The polyethylene glycol 400 and triacetin are added to the cellulose acetate solution and stirred until a clear solution is obtained. The tablet is coated by spraying the clear coating solution onto the seal coated tablets in a fluidized bed coater employing the following conditions: product temperature of 16–22° C.; atomization pressure of approximately three bars; and spray rate of 120–150 ml/min.

(d) Laser Drilling

The coated tablets were laser drilled two holes (one hole on each side of the tablet).

EXAMPLE 2

A controlled release tablet containing 850 mg of metformin HCl and having the following formula is prepared as follows:

| I. Core | |
|---|---|
| Ingredients | Amount (mg/tab) |
| Metformin HCl | 850.0 |
| Povidone[3], USP | 61.1 |
| Sodium Lauryl Sulfate | 43.9 |
| Magnesium Stearate | 4.8 |

3approximate molecular weight = 1,000,000; dynamic viscosity (10% w/v solution at 20° C.) = 300–700 m Pa s.

(a) Granulation

The metformin HCl and sodium lauryl sulfate are delumped by passing them through a 40 mesh screen and collecting them in a clean, polyethylene-lined container. The povidone, K-90-F is dissolved in purified water. The delumped metformin HCl and sodium lauryl sulfate are then added to a top-spray fluidized bed granulator and granulated by spraying with the binding solution of povidone under the following conditions: inlet air temperature of 50–70° C.; atomization air pressure of 1–3 bars; and spray rate of 10–100 ml/min.

Once the binding solution is depleted, the granules are dried in the granulator until the loss on drying is less than 2%. The dried granules are passed through a Comil equipped with the equivalent of an 18 mesh screen.

(b) Tableting

The magnesium stearate is passed through a 40 mesh stainless steel screen and blended with the metformin HCl granules for approximately five (5) minutes. After blending, the granules are compressed on a rotary press fitted with 15/32" round standard concave punches.

(c) Seal Coating (Optional)

The core tablet is seal coated with an Opadry material or other suitable water-soluble material by first dissolving the Opadry material, preferably Opadry Clear (YS-1-7006), in purified water. The Opadry solution is then sprayed onto the core tablet using a pan coater under the following conditions: exhaust air temperature of 38–42° C.; atomization pressure of 28–40 psi; and spray rate of 10–15 ml/min. The Opadry Clear of the coating constitutes about 11.5 mg/tablet.

| II. Sustained Release Coating | |
|---|---|
| Ingredients | Amount (mg/tablet) |
| Cellulose Acetate (398-10)[2] | 24.0 |
| Triacetin | 1.4 |
| PEG 400 | 2.8 |

[2]acetyl content 39.3–40.3%

The cellulose acetate is dissolved in acetone while stirring with a homogenizer. The polyethylene glycol 400 and triacetin are added to the cellulose acetate solution and stirred until a clear solution is obtained. The tablet is coated by spraying the clear coating solution onto the seal coated tablets in a fluidized bed coater employing the following conditions: product temperature of 16–22° C.; atomization pressure of approximately three bars; and spray rate of 120–150 ml/min.

(d) Laser Drilling

The coated tablets were laser drilled two holes (one hole on each side of the tablet).

EXAMPLE 3

A controlled release tablet containing 1000 mg of metformin HCl and having the following formula is prepared as follows:

| I. Core | |
|---|---|
| Ingredients | Amount (mg/tablet) |
| Metformin HCl | 1000.0 |
| Povidone[3], USP | 71.9 |
| Sodium Lauryl Sulfate | 51.7 |
| Magnesium Stearate | 5.6 |

[3]approximate molecular weight = 1,000,000; dynamic viscosity (10% w/v solution at 20° C.) = 300–700 m Pa s.

(a) Granulation

The metformin HCl and sodium lauryl sulfate are delumped by passing them through a 40 mesh screen and collecting them in a clean, polyethylene-lined container. The povidone, K-90-F is dissolved in purified water. The delumped metformin HCl and sodium lauryl sulfate are then added to a fluidized bed granulator and granulated by spraying with the binding solution of povidone under the following conditions: inlet air temperature of 50–70° C.; atomization air pressure of 1–3 bars; and spray rate of 10–100 ml/min.

Once the binding solution is depleted, the granules are dried in the granulator until the loss on drying is less than 2%. The dried granules are passed through a Comil equipped with a screen equivalent to 18 mesh.

(b) Tableting

The magnesium stearate is passed through a 40 mesh stainless steel screen and blended with the metformin HCl granules for approximately five (5) minutes. After blending, the granules are compressed on a rotary press fitted with ½" round standard concave punches.

(c) Seal Coating (Optional)

The core tablet is seal coated with an Opadry material or other suitable water-soluble material by first dissolving the Opadry material, preferably Opadry Clear (YS-1-7003), in purified water. The Opadry solution is then sprayed onto the core tablet using a pan coater under the following conditions: exhaust air temperature of 38–42° C.; atomization pressure of 28–40 psi; and spray rate of 10–15 ml/min. The core tablet is coated with the sealing solution until the tablet is coated with 23.0 mg/tablet of the Opadry material.

| II. Sustained Release Coating | |
|---|---|
| Ingredients | Amount (mg/tablet) |
| Cellulose Acetate (398-10)[2] | 19.0 |
| Triacetin | 1.1 |
| PEG 400 | 2.2 |

[2]acetyl content 39.3–40.3%

The cellulose acetate is dissolved in acetone while stirring with a homogenizer. The polyethylene glycol 400 and triacetin are added to the cellulose acetate solution and stirred until a clear solution is obtained. The tablet is coated by spraying the clear coating solution onto the seal coated tablets in a fluidized bed coater employing the following conditions: product temperature of 16–22° C.; atomization pressure of approximately three bars; and spray rate of 120–150 ml/min.

(d) Laser Drilling

The coated tablets were laser drilled two holes (one hole on each side of the tablet).

(e) Color Coating (Optional)

Subsequent to the sustained release coating, the laser drilled tablet is coated with a color coating using Opadry White (24 mg/tablet) and waxed with Candelilla wax powder (0.4 mg/tablet).

Clinical Studies

Study 1

In study 1, a total of twelve (12) healthy subjects (six males, six females) were randomized to receive either a single oral dose of metformin XT, 850 mg, prepared in accordance with Example 2 or b.i.d. doses of GLUCOPHAGE in assigned study periods which consisted of one of the following groups: Group A—metformin XT (2×850 mg tablets) taken at approximately 8:00 a.m., immediately following breakfast, Group B—metformin XT (2×850 mg tablets) taken at approximately 6:00 p.m., immediately following dinner; and Group C—GLUCOPHAGE (1×850 mg tablet) taken at approximately 8:00 a.m., immediately following breakfast, and at approximately 6:00 p.m., immediately following dinner. Each drug administration was separated by a washout period of seven days. In this study, one male subject was removed from the study prior to Period II due to non-treatment-related mononucleosis. Thus, 11 (five males and six females) subjects completed the study.

For metformin XT, plasma samples were obtained from subjects at 0 (predose), 1, 2, 3, 4, 5, 6, 8, 10, 12, 14, 16, and 24 hour(s) after dosing. For GLUCOPHAGE, plasma samples were obtained from subjects at 0 (predose), 1, 2, 3, 4, 5, 6, 8, 10, 11, 12, 13, 14, 15, 16, 18, 20, 22, and 24 hour(s) after the first dose in the morning. Plasma concentrations of metformin were determined using a validated HPLC method. The lower quantitation limit of this method is 10 ng/ml. Mean plasma concentration-time profiles are shown in FIG. 1 and mean values of pharmacokinetic parameters of metformin obtained from this study are presented in Table 1.

TABLE 1

Mean (±SD, n = 11) values of pharmacokinetic parameters of metformin (Example 2) in 11 healthy subjects (metformin XT, 2 × 850 mg q.d. or GLUCOPHAGE, 1 × 850 mg b.i.d.)

| Treatment | $AUC_{0-\infty}$ (ng-hr/ml) | $C_{max}$ (ng/ml) | $T_{max}$ (hr.) | $T_{lag}$ (hr) | $t_{½}$ (hr) | Geometric Mean Ratio* $AUC_{0-\infty}$ | $C_{max}$ |
|---|---|---|---|---|---|---|---|
| Metformin XT after breakfast | 18156 (4183) | 2045 (567) | 6 (2) | 0.18 (0.40) | 4.4 (0.7) | 1.00 | 1.36 |
| Metformin XT after dinner | 18277 (2961) | 1929 (333) | 7 (2) | 0.09 (0.30) | 3.6 (0.8) | 1.02 | 1.32 |
| GLUCOPHAGE | 18050 (3502) | 1457 (217) | 5 (3) | 0 (0) | 3.5 (0.9) | — | — |

*Ratio = Metformin XT/GLUCOPHAGE

As shown in FIG. 1 and Table 1, when metformin XT was administered immediately after either breakfast or dinner, the relative bioavailability of metformin XT formulation to GLUCOPHAGE is approximately 100%.

The results of study 1 were used to calculate the approximate degree of fluctuation ($C_{max}$–$C_{min}$/$C_{avg}$) of the formulations.

The $C_{max}$ was directly obtained from the study (see Table 1). The $C_{avg}$ was obtained by dividing the AUC value by the dosing interval, i.e. 24 hours. The value for $C_{min}$ was extrapolated from FIG. 1.

The results are set forth in Table 2 below:

TABLE 2

Mean (±SD, n = 12) values of pharmacokinetic parameters of metformin XT in 12 healthy subjects (metformin XT, 2 × 850 mg q.d. and GLUCOPHAGE, 850 mg b.i.d.)

| Treatment | $AUC_{0-\infty}$ (ng-hr/ml) | $C_{max}$ (ng/ml) | $C_{min}$ (ng/ml) | $C_{avg}$ (ng/ml) | Degree of Fluctuation |
|---|---|---|---|---|---|
| Metformin XT after breakfast | 18156 (4183) | 2045 (567) | 143 | 756 | 2..51 |
| Metformin XT after dinner | 18277 (2961) | 1929 (333) | 107 | 761 | 2.39 |
| GLUCOPHAGE | 18050 (3502) | 1457 (217) | 214 (at 24 hours) | 752 | 1.65 |
|  |  |  | 393 (between doses) | 752 | 1.41 |

As shown in FIG. 1 and Table 2, a single administration of the metformin XT formulation provides a higher mean fluctuation index in the plasma than a substantially equal dose of Glucophage administered as two equal divided doses, one divided dose at the start of the dosing interval and the other divided dose administered 12 hours later.

Study 2

The study design of Study 2 is the same as Study 1 except for the formulation and the dose (4×500 mg q.d., total dose 2000 mg, for metformin XT prepared according to Example 1 and 2×500 mg b.i.d., total dose 2000 mg, for GLUCOPHAGE in the second study). In this study, 12 healthy volunteers (five males and seven females) were randomized to receive treatments and completed the study. Mean plasma concentration-time profiles and mean values of pharmacokinetic parameters of metformin obtained from this study are presented in FIG. 2 and Table 3.

Figure 2:
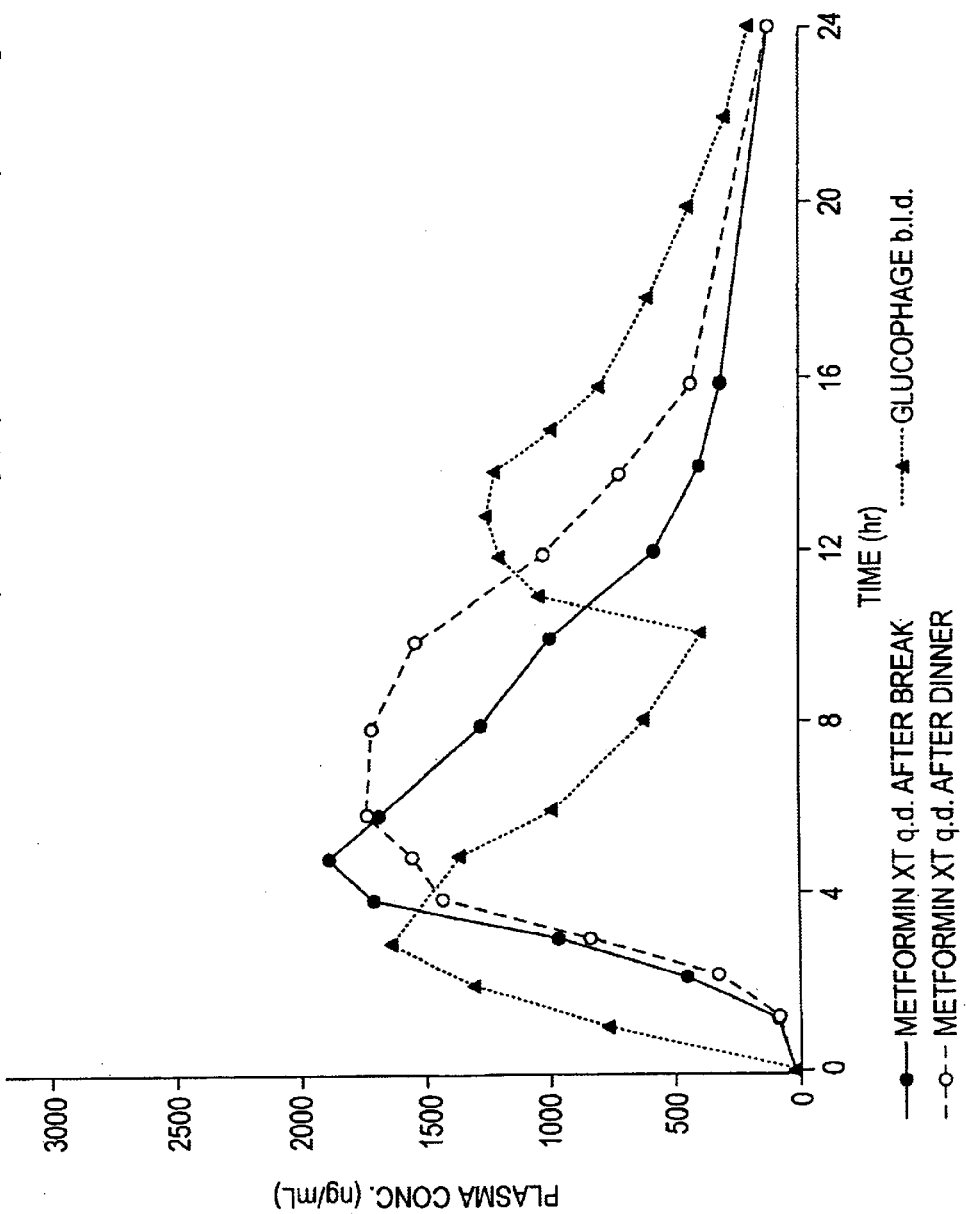
FIG. 2 is a graph showing the relative bioavailability of the metformin XT formulation of Example 1 (500 mg) to GLUCOPHAGE® for Clinical Study 3.

As shown in FIG. 2 and Table 3, when the metformin XT formulation (500 mg) was administered immediately after dinner, the relative bioavailability of this formulation to GLUCOPHAGE is approximately 100%, while the mean $C_{max}$ value is about the same. The relative bioavailability of metformin XT, however, is approximately 80% when administered immediately after breakfast. A prolonged profile, together with later $T_{max}$ and similar $C_{max}$ of metformin following administration of metformin XT immediately after dinner compared to GLUCOPHAGE indicated that metformin was released in vivo in a sustained fashion (FIG. 2).

TABLE 3

Mean (±SD, n = 12) values of pharmacokinetic parameters of metformin of Example 1 in 12 healthy subjects (metformin XT, 4 × 500 mg q.d. or GLUCOPHAGE, 2 × 500 mg b.i.d.)

| Treatment | $AUC_{0-\infty}$ (ng-hr/ml) | $C_{max}$ (ng/ml) | $T_{max}$ (hr) | $T_{lag}$ (hr) | $t_{½}$ (hr) | Geometric Mean Ratio* $AUC_{0-\infty}$ | $C_{max}$ |
|---|---|---|---|---|---|---|---|
| Metformin XT after breakfast | 17322 (4984) | 2127 (545) | 5 (1) | 0 (0) | 6.1 (1.8) | 0.80 | 1.15 |
| Metformin XT after dinner | 20335 (4360) | 2053 (447) | 7 (2) | 0.08 (0.29) | 3.9 (0.6) | 0.96 | 1.12 |
| GLUCOPHAGE | 21181 (4486) | 1815 (302) | 4 (3) | 0 (0) | 3.6 (0.8) | — | — |

*Ratio = Metformin XT/GLUCOPHAGE

The results of study 2 were used to calculate the approximate degree of fluctuation of the formulations in accordance with the calculations used in study 1 (using FIG. 2 to obtain the extrapolated value for $C_{min}$).

The results are set forth in Table 4 below:

TABLE 4

Mean (±SD, n = 12) values of pharmacokinetic parameters of metformin XT in 12 healthy subjects (metformin XT, 4 × 500 mg q.d. and GLUCOPHAGE, 2 × 500 mg b.i.d.)

| Treatment | $AUC_{0-\infty}$ (ng-hr/ml) | $C_{max}$ (ng/ml) | $C_{min}$ (ng/ml) | $C_{avg}$ (ng/ml) | Degree of Fluctuation |
|---|---|---|---|---|---|
| Metformin XT after breakfast | 17322 (4984) | 2127 (545) | 143 | 721 | 2.9 |
| Metformin XT after dinner | 20335 (4360) | 2053 (447) | 143 | 847 | 2.25 |
| GLUCOPHAGE | 21181 (4486) | 1815 (302) | 214 (at 24 hours) | 882 | 1.8 |
|  |  |  | 357 (between doses) | 882 | 1.65 |

As shown in FIG. 2 and Table 4, a single administration of the metformin XT formulation provides a higher mean fluctuation index in the plasma than an equivalent dose of Glucophage administered as two equal divided doses, one divided dose at the start of the dosing interval and the other divided dose administered 12 hours later.

Study 3

In Study 3, a multiple-dose, open-label, one-period study was conducted to evaluate the short-term tolerability and steady-state pharmacokinetics of the 500 mg metformin XT formulation used in Study 2. In this study, eight healthy volunteers (four males and four females) were randomized to receive 2000 mg of metformin XT (4×500 mg tablets) at approximately 6:00 p.m., immediately following dinner, for 14 days.

Blood samples were obtained from each subject at 0 (predose), 1, 2, 3, 4, 5, 6, 8, 10, 12, 14, 16 and 24 hour(s) following the first dose on Day 1 and at 0 (predose), 1, 2, 3, 4, 5, 6, 8, 10, 12, 14, 16, 24, 38 and 48 hour(s) following the last dose on Day 14. Blood samples were also drawn from each subject immediately prior to dosing on Days 10–13. Urine samples were collected from each subject at the following time intervals: six hours prior to the first dose; 0–6, 6–12 and 12–24 hours after the first dose; and 0–6, 6–12, 12–24 and 24–48 hours after the last dose.

Mean plasma profiles and values of pharmacokinetic parameters of metformin are presented in Table 5 below:

TABLE 5

Mean Pharmacokinetic Parameters (Example 1)

|  | $C_{max}$ | $T_{max}$ | $AUC_{0-24\ hr}$ (ng · hr/ml) |
|---|---|---|---|
| Day 1 | | | |
| Mean | 2435 | 6.9 | 22590 |
| SD | 630 | 1.9 | 3626 |
| Day 14 | | | |
| Mean | 2288 | 6.9 | 24136 |
| SD | 736 | 2.5 | 7996 |

Figure 3:
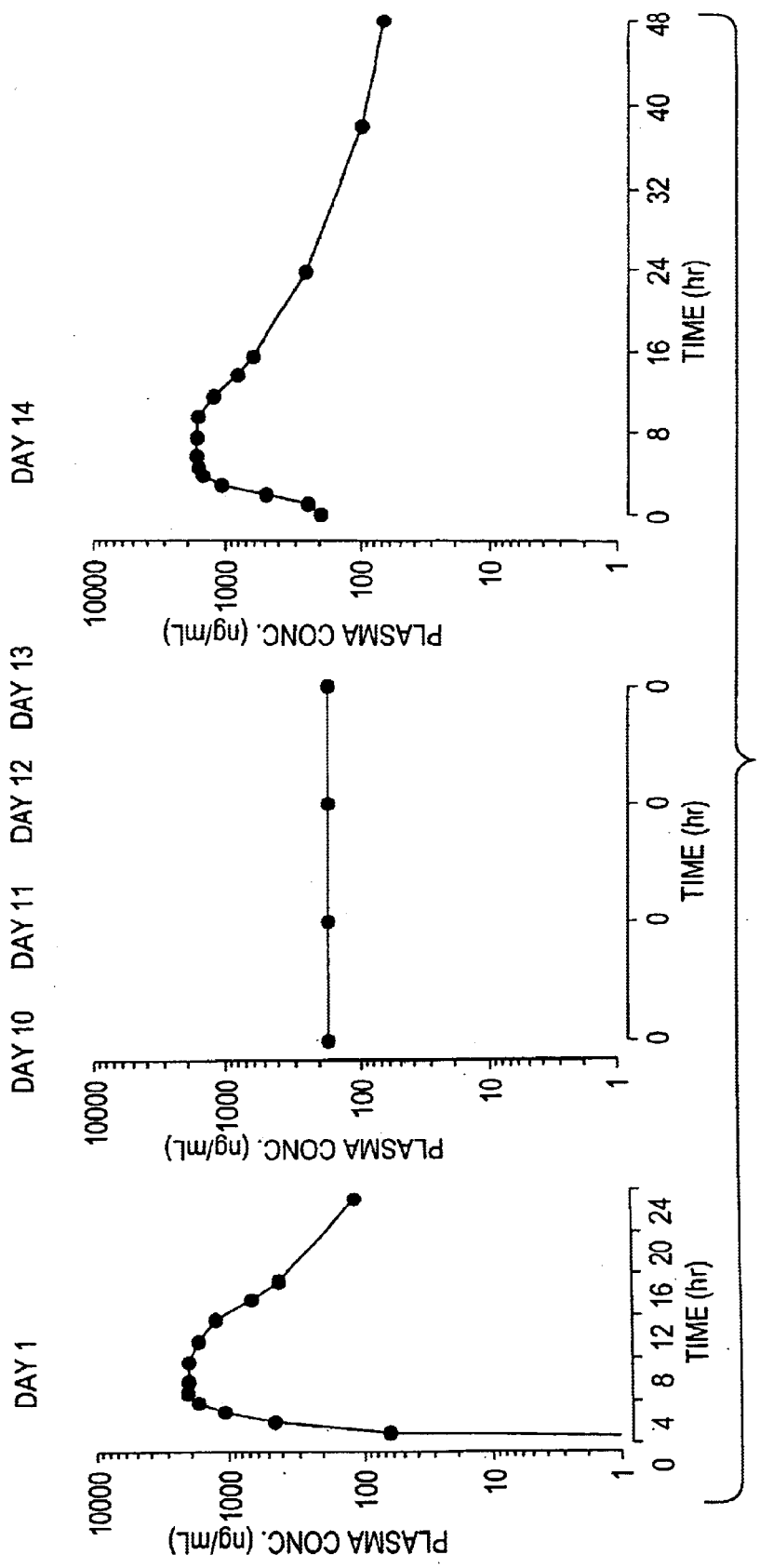
FIG. 3 is a graph showing the difference in plasma concentration-time profiles of metformin in eight healthy volunteers between Day 1 and Day 14 dosing following oral administration of the metformin XT formulation of Example 1, 4×500 mg q.d. for 14 days for Clinical Study 4.

Following oral administration of metformin XT, 4×500 mg q.d., for 14 days, there was little or no difference in plasma concentration-time profiles of metformin in eight healthy volunteers between Day 1 and Day 14 dosing (FIG. 3). On average, trough plasma concentrations of metformin were nearly constant, ranging from 188.8 to 205.1 ng/ml on Days 10–14, indicating that the steady state of metformin was attained rapidly. The mean accumulation ratio was 1.01, indicating that the once-daily dose regimen of metformin XT results in no accumulation.

Following oral administration of a single dose (4×500 mg) of metformin XT, approximately 31% of the dose was excreted in the urine within the first 24 hours. On average, the renal clearance of metformin was 366 ml/min. A slightly higher renal clearance (454 ml/min) was found after multiple-dose administration of 4×500 mg q.d. of metformin XT.

Gastrointestinal symptoms (diarrhea, nausea, vomiting, abdominal bloating, flatulence and anorexia) are the most common adverse reactions to GLUCOPHAGE. In controlled trials, GLUCOPHAGE was started at low, nontherapeutic doses and gradually titrated to higher doses. In spite of this gradual titration, GLUCOPHAGE was discontinued due to gastrointestinal reactions in approximately 4% of patients. In contrast, in the multiple-dose study, metformin XT begun at a therapeutic initial dose of 2000 mg once daily with dinner was well tolerated by all healthy volunteers. Diarrhea and nausea were the most common gastrointestinal reactions probably or possibly related to metformin XT. These reactions, however, were either mild or moderate. This suggests that it may be possible to initiate metformin XT treatment with effective doses rather than using the slow titration from non-therapeutic doses required for GLUCOPHAGE.

Study 4

Study 4 was a study designed to evaluate the safety, tolerability, pharmacokinetics and pharmacodynarnics of metformin XT compared to GLUCOPHAGE after multiple-dose treatment in patients with NIDDM. Metformin XT tablets prepared according to Example 3 were used in this study. This study had a single-center, randomized, two-way crossover design. A total of 24 NIDDM patients who were on a stable dose of GLUCOPHAGE, between 1000 and 2550 mg/day, for at least 12 weeks were selected for the study. A Pretreatment Period of at least 3 weeks preceded randomization to study treatment. At the start of the Pretreatment Period, all patients stopped taking any other hypoglycemic agents besides GLUCOPHAGE, and the GLUCOPHAGE dose was adjusted to 1000 mg b.i.d. (with breakfast and with dinner). Following the pretreatment period, patients began Treatment Period I, which lasted 4 weeks. During Period I, a total of 12 patients were randomized to receive two 1000-mg metformin XT tablets q.d. (immediately after dinner), at approximately 6:00 p.m., and 12 were randomized to receive one 1000-mg GLUCOPHAGE tablet b.i.d. (immediately after breakfast and immediately after dinner). Imediately following Period I, each patient was switched to the alternate medication for 4 weeks in Period II. There was no washout between treatment periods.

Plasma metformin concentrations were determined over a 24-hour period at the end of Treatment Periods I and II as follows: immediately prior to dosing and at 1, 2, 3, 4, 5, 6, 8, 10, 12, 14, 15, 16, 17, 18, 19, 20, 22, and 24 hours after the evening dose. One subject withdrew from the study for personal reasons after two weeks of treatment in Treatment Period I, thus pharmacokinetic data were obtained from 23 patients.

Figure 4:
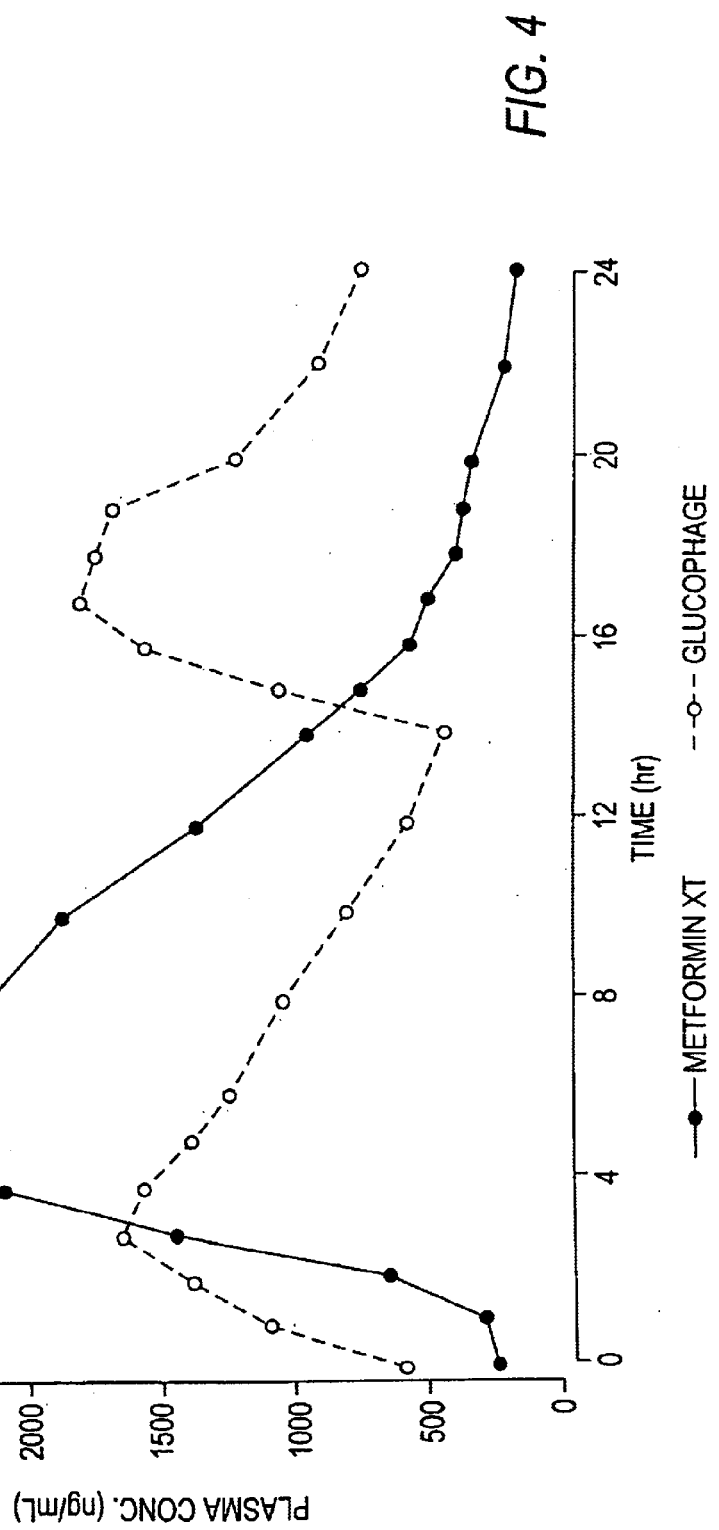
FIG. 4 is a graph showing the mean plasma profiles and values of pharmacokinetic parameters of the metformin XT formulation of Example 3 for Clinical Study 5.
Figure 5:
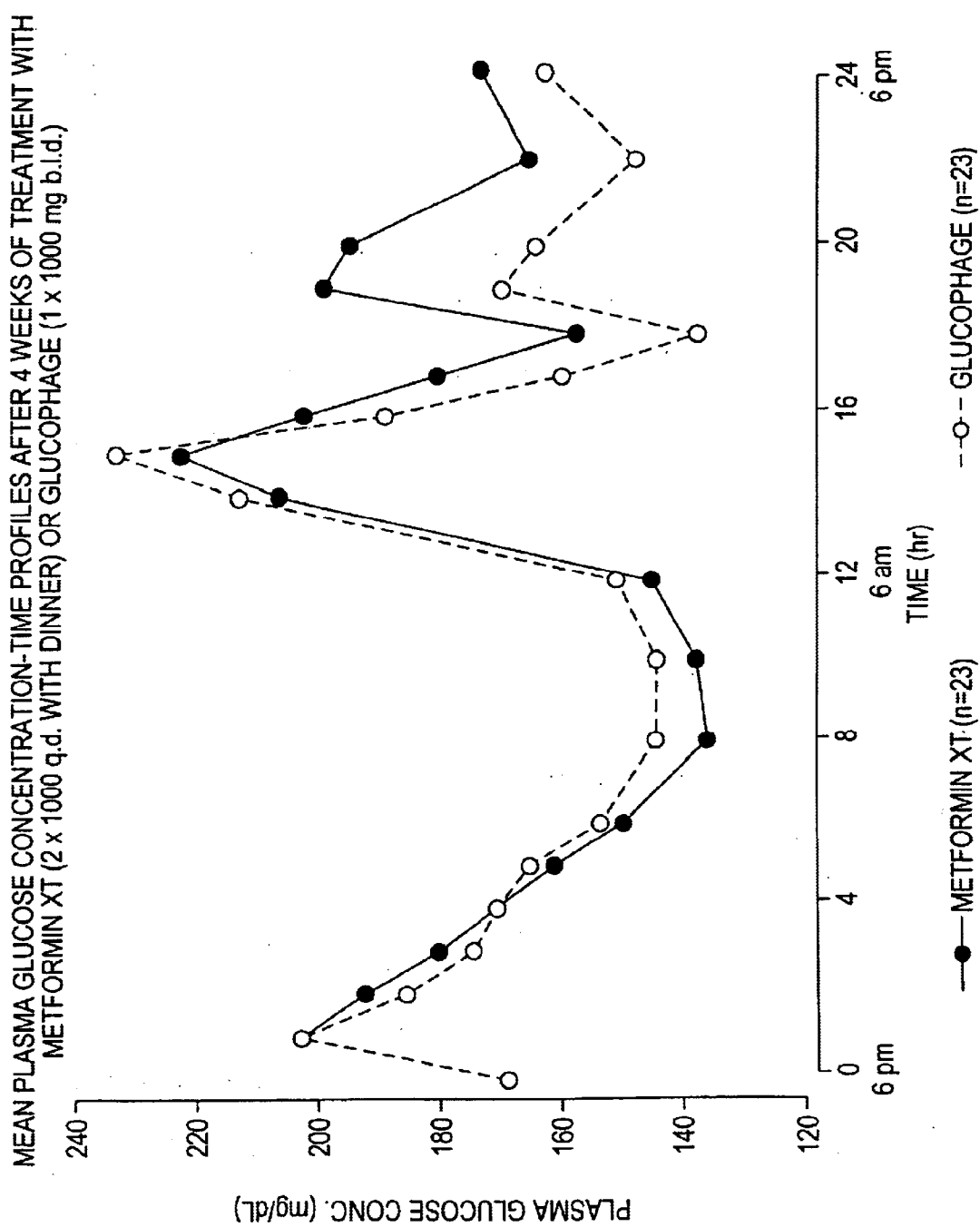
FIG. 5 is a graph showing the mean plasma glucose concentration-time profiles after 4 weeks of treatment with the metformin XT formulation of Example 3 and GLUCOPHAGE® for Clinical Study 5.
Figure 6:
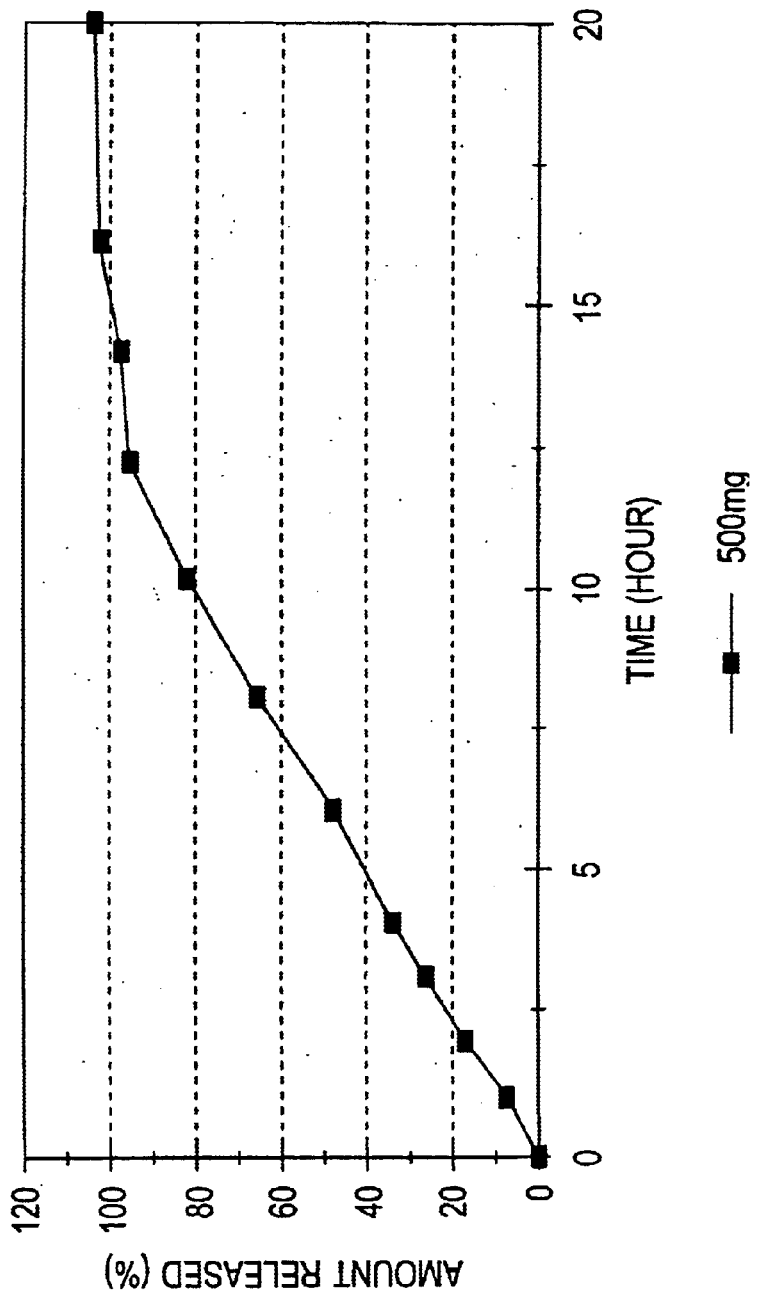
FIG. 6 is a graph showing the dissolution profile of a 500 mg controlled release metformin formulation of Example 1 of the present invention.
Figure 7:
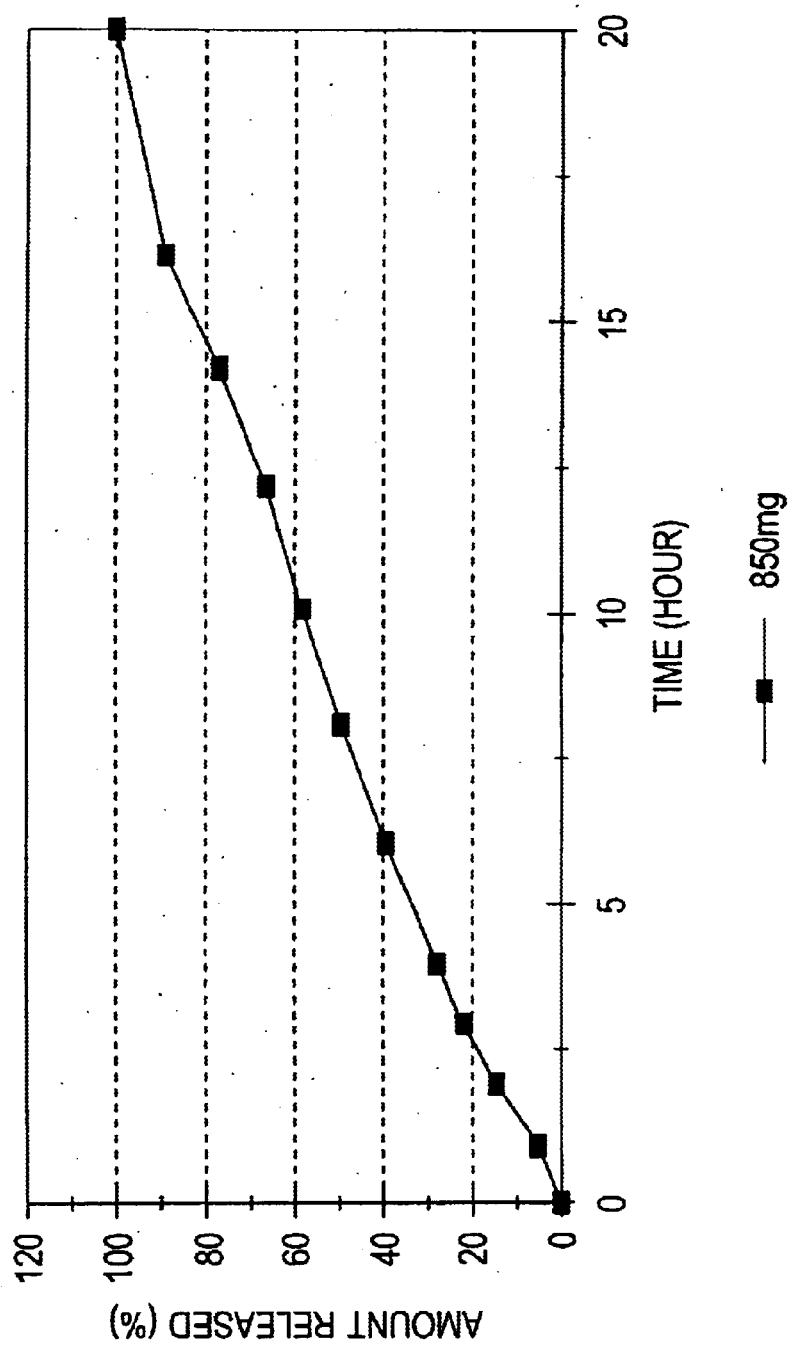
FIG. 7 is a graph showing the dissolution profile of a 850 mg controlled release metformin formulation of Example 2 of the present invention.
Figure 8:
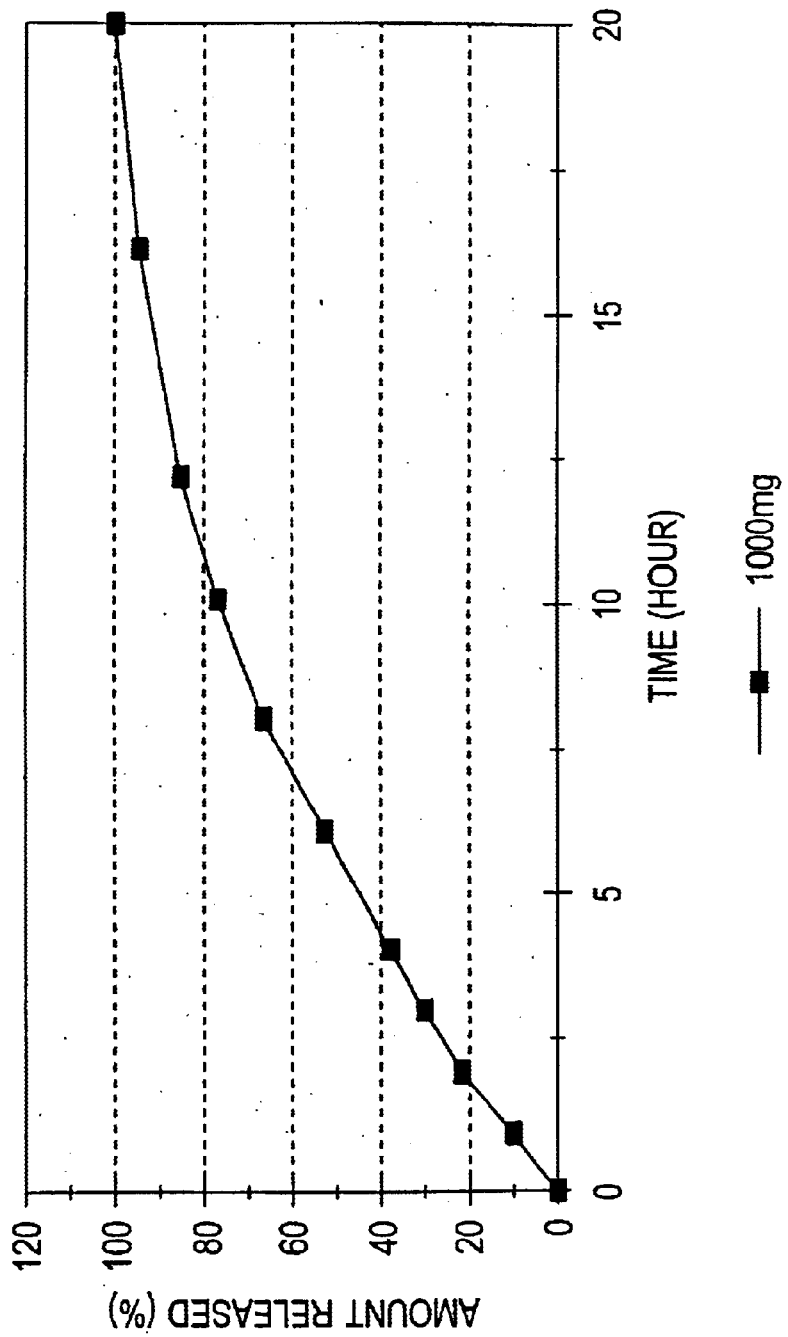
FIG. 8 is a graph showing the dissolution profile of a 1000 mg controlled release metformin formulation of Example 3 of the present invention.

Mean plasma profiles and values of pharmacokinetic parameters of metformin are presented in FIG. 4 and Table 6. As shown in FIG. 4 and Table 6, when metformin XT was administered immediately after dinner, the bioavailability of metformin XT relative to GLUCOPHAGE at steady state is close to 100%. Although the dose of metformin XT was twice as large as the dose of GLUCOPHAGE at dinner, the mean $C_{max}$ value was only 32% higher.

TABLE 6

Mean (±SD) values of pharmacokinetic parameters of metformin of Example 3 in 23 NIDDM patients (metformin XT, 2 × 1000 mg q.d. with dinner or GLUCOPHAGE, 1 × 1000 mg b.i.d.)

| Treatment | $AUC_{0-24hr}$ (ng·hr/ml) | $C_{max}$ (ng/ml) | $T_{max}$ (hr) | $T_{lag}$ (hr) | $t_{½}$ (hr) | Geometric Mean Ratio* $AUC_{0-24hr}$ | $C_{max}$ |
|---|---|---|---|---|---|---|---|
| Metformin XT after dinner | 26818 (7052) | 2849 (797) | 6 (2) | 0 (0) | 5.4 | 0.96 | 1.32 |
| GLUCOPHAGE | 27367 (5759) | 2131 (489) | 14 (6) | 0 (0) | 4.4 | — | — |

*Ratio = Metformin XT/GLUCOPHAGE

When the metformin XT was administered immediately after dinner, the bioavailability of metformin XT relative to GLUCOPHAGE at steady state was close to 100%. However, when metformin XT was administered immediately after breakfast, the corresponding relative bioavailability of metformin XT was approximately 80%. The safety profile of metformin XT, 2000 mg given once daily either after dinner or after breakfast was comparable to that of an equal dose of GLUCOPHAGE given b.i.d. The efficacy profile of metformin XT, 2000 mg given once daily after dinner was similar to that of an equal dose of GLUCOPHAGE given b.i.d. The efficacy of metformin XT, 2000 mg given once daily after breakfast, however, appeared to be comparable to or slightly less than that of GLUCOPHAGE given b.i.d.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

What is claimed is:

1. A controlled release oral dosage form for the reduction of serum glucose levels in human patients with NIDDM, comprising an effective dose of metformin or a pharmaceutically acceptable salt thereof and a controlled-release carrier to control the release of said metformin or pharmaceutically acceptable salt thereof from said dosage form, said dosage form being suitable for providing once-a-day oral administration of the metformin or pharmaceutically acceptable salt thereof, wherein following oral administration of a single dose, the dosage form provides a mean time to maximum plasma concentration ($T_{max}$) of the metformin from 5.5 to 7.5 hours after administration following dinner.

2. The controlled release oral dosage form of claim 1, which provides a mean time to maximum plasma concentration ($T_{max}$) of metformin at from 6.0 to 7.0 hours after the administration of the dose.

3. The controlled release oral dosage form of claim 1, which provides a mean time to maximum plasma concentration ($T_{max}$) of metformin at from 5.5 to 7.0 hours after the administration of the dose.

4. The controlled release oral dosage form of claim 1, which exhibits the following dissolution profiles when tested in a USP type 2 apparatus at 75 rpm in 900 ml of simulated intestinal fluid (pH 7.5 phosphate buffer) and at 37 C:

0–30% of the metformin or salt thereof is released after 2 hours;

10–45% of the metformin or salt thereof is released after 4 hours;

30–90% of metformin or salt thereof is released after 8 hours;

not less than 50% of the metformin or salt thereof is released after 12 hours;

not less than 60% of the metformin or salt thereof is released after 16 hours; and not less than 70% of the metformin or salt thereof is released after 20 hours.

5. The controlled release oral dosage form of claim 1, which exhibits the following dissolution profiles when tested in a USP type 2 apparatus at 75 rpm in 900 ml of simulated intestinal fluid (pH 7.5 phosphate buffer) and at 37 C:

0–25% of the metformin or salt thereof is released after 2 hours;

20–40% of the metformin or salt thereof is released after 4 hours;

45–90% of the metformin or salt thereof is released after 8 hours;

not less than 60% of the metformin or salt thereof is released after 12 hours;

not less than 70% of the metformin or salt thereof is released after 16 hours; and not less than 80% of the metformin or salt thereof is released after 20 hours.

6. The controlled release oral dosage form of claim 1, which provides a width at 50% of the height of a mean plasma concentration/time curve of the metformin from about 4.5 to about 13 hours.

7. The controlled release oral dosage form of claim 1, which provides a width at 50% of the height of a mean plasma concentration/time curve of the metformin from about 5.5 to about 10 hours.

8. The controlled release oral dosage form of claim 1, which provides a mean maximum plasma concentration ($C_{max}$) of metformin which is more than about 7 times the mean plasma level of said metformin at about 24 hours after the administration.

9. The controlled release oral dosage form of claim 1, which provides a mean maximum plasma concentration ($C_{max}$) of metformin which is from about 7 times to about 14 times the plasma level of said metformin at about 24 hours after administration.

10. The controlled release oral dosage form of claim 1 which provides a mean maximum plasma concentration ($C_{max}$) of metformin which is from about 8 times to about 12 times the plasma level of said metformin at about 24 hours after administration.

11. The controlled release oral dosage form of claim 1 which provides a mean maximum plasma concentration ($C_{max}$) of metformin from about 1500 ng/ml to about 3000 ng/ml, based on administration of a 2000 mg once-a-day dose of metformin.

12. The controlled release oral dosage form of claim 1, which provides a mean maximum plasma concentration ($C_{max}$) of metformin from about 1700 ng/ml to about 2000 ng/ml, based on administration of a 2000 mg once-a-day dose of metformin.

13. The controlled release oral dosage form of claim 1 which provides a mean $AUC_{0-24hr}$ of at least 80% of the mean $AUC_{0-24}$ provided by administration of an immediate release reference standard twice a day, wherein the daily dose of the reference standard is substantially equal to the once-a-day dose of metformin administered in the controlled release oral dosage form.

14. The controlled release oral dosage form of claim 1 which provides a mean $AUC_{0-24hr}$ of at least 90% of the mean $AUC_{0-24}$ provided by administration of an immediate release reference standard twice a day, wherein the daily dose of the reference standard is substantially equal to the once-a-day dose of metformin administered in the controlled release oral dosage form.

15. The controlled release oral dosage form of claim 1 which provides a mean $AUC_{0-24hr}$ from about 17200 ng.hr/ml to about 33900 ng.hr/ml, based on administration of a 2000 mg once-a-day dose of metformin.

16. The controlled release oral dosage form of claim 1 which provides a mean $AUC_{0-24hr}$ from about 17200 ng.hr/ml to about 26500 ng.hr/ml, based on administration of a 2000 mg once-a-day dose of metformin.

17. The controlled release oral dosage form of claim 1 which provides a mean $AUC_{0-24hr}$ from about 19800 ng.hr/ml to about 33900 ng.hr/ml, based on administration of a 2000 mg once-a-day dose of metformin.

18. The controlled release oral dosage form of claim 1 which provides a mean $AUC_{0-\infty}$ of 18277±2961 ng.hr/ml and a mean $C_{max}$ of 1929±333 ng/ml, for administration of a 1700 mg once-a-day dose of metformin after an evening meal.

19. The controlled release oral dosage form of claim 1 which provides a mean $AUC_{0-\infty}$ of 20335±4360 ng.hr/ml and a mean $C_{max}$ of from 2053±447 ng/ml, for administration of a 2000 mg once-a-day dose of metformin after an evening meal.

20. The controlled release oral dosage form of claim 1 which provides a mean $AUC_{0-24}$ of 26818±7052 ng.hr/ml and a mean $C_{max}$ of 2849±797 ng/ml, for, administration of a 2000 mg once-a-day dose of metformin after an evening meal.

21. The controlled release oral dosage form of claim 1 which provides a mean $AUC_{0-24}$ of 22590±3626 ng.hr/ml and a mean $C_{max}$ of 2435±630 ng/ml on the first day of administration and a mean $AUC_{0-24}$ of 24136±7996 ng.hr/ml and a mean $C_{max}$ of 2288±736 ng/ml on the $14^{th}$ day of administration, for administration of a 2000 mg once-a-day dose of metformin after an evening meal.

22. The controlled release oral dosage form of claim 12 which provides a mean $t_{1/2}$ from 2.8 to 4.4.

23. The controlled release oral dosage form of claim 6, which provides a mean time to maximum plasma concentration ($T_{max}$) of metformin from 6.0 to 7.0 hours after the administration.

24. The controlled release oral dosage form of claim 6, which provides a mean time to maximum plasma concentration ($T_{max}$) of metformin from 5.5 to 7.0 hours after administration.

25. The controlled release dosage form of claim 1, wherein the metformin or pharmaceutically acceptable salt thereof is provided by at least one controlled-release tablet, said tablet comprising:
   (a) a core comprising:
      (i) the metformin or a pharmaceutically acceptable salt;
      (ii) optionally a binding agent; and
      (iii) optionally an absorption enhancer;
   (b) a membrane coating surrounding the core; and
   (c) at least one passageway in the membrane.

* * * * *